United States Patent [19]

Obrero et al.

[11] Patent Number: 4,834,790

[45] Date of Patent: May 30, 1989

[54] METHOD OF TREATING PINEAPPLES TO INHIBIT OPENING OF THE PINEAPPLE FLOWERS

[75] Inventors: Faustino P. Obrero; Wilfred H. Schnitzler, both of Manila, Philippines

[73] Assignee: Del Monte Corporation, San Francisco, Calif.

[21] Appl. No.: 948,236

[22] Filed: Dec. 31, 1986

[51] Int. Cl.⁴ .................. A01N 31/02; A01N 41/04; A01N 37/02
[52] U.S. Cl. .......................... 71/124; 71/98; 71/103; 71/113; 71/DIG. 1
[58] Field of Search ................ 71/124, DIG. 1

[56] References Cited

U.S. PATENT DOCUMENTS

| | | | |
|---|---|---|---|
| 2,242,429 | 5/1941 | Johnson et al. | 71/127 |
| 3,741,746 | 6/1973 | Marrese | 71/72 |
| 4,001,002 | 1/1977 | Barba | 71/65 |

FOREIGN PATENT DOCUMENTS 1505331  3/1978  United Kingdom .......... 71/DIG. 1

OTHER PUBLICATIONS

Tjra, "Surfactants Remove Flower Buds from Lilium Longiflorum", Hort. Science, vol. 11 (3), pp. 199-200 (1976).
Roberts et al., "New Lily Deflowering Treatment Shows, etc.," Flor. Review 151: 25-26 (1972).
Cunha et al., "Growth Regulators Effects on flower Opening, etc." C. A., 94:59685W, pp. 203-204 (1981).

*Primary Examiner*—Glennon H. Hollrah
*Assistant Examiner*—Susan Treanor
*Attorney, Agent, or Firm*—Richard Kornutik

[57] ABSTRACT

Pineapple plants are chemically treated in the field with effective amounts of an aqueous solution of a nonionic or anionic surfactant to inhibit opening of the pineapple flowers, so that the susceptibility of the pineapple plant to fruit disease is reduced.

9 Claims, No Drawings

METHOD OF TREATING PINEAPPLES TO INHIBIT OPENING OF THE PINEAPPLE FLOWERS

FIELD OF THE INVENTION

This invention pertains to a method for reducing the susceptability of pineapple plants to fruit diseases by chemical treatment to inhibit opening of the pineapple flowers.

BACKGROUND OF THE INVENTION

Pineapple fruits are known to have about 150 to 200 flowers which open acropetally in batches of 2 to 15 flowers a day. Generally, the flowering period for each fruit is completed in about 21 days. Because the open flowers serve as the main entrance points for many of the microorganisms causing pineapple fruit diseases, the pineapple plant becomes more disease prone as flowering proceeds.

Consequently, efforts have been directed towards developing pineapple varieties having closed flowers, which are more resistant to pineapple fruit diseases. To date, the plant growth regulator ethrel (2-chloroethyl phosphoric acid) is the only generally known compound for preventing pineapple flowers from opening. During decomposition, ethrel releases ethylene, a growth regulator that occurs naturally in most plants.

Unfortunately, in order to be used most effectively, ethrel must be applied every other day during the flowering period, for a total of about 10 applications. Thus, a method that is more effective and less costly has been desired.

The present invention pertains to a method which meets these criteria, and which uses certain surfactants described more particularly below.

At this point, it may be noted that certain surfactants have been reported as being effective abortive agents for the flower buds of Easter lilies. (See, B. Tjia, "Surfactants Removes Flower Buds from Lilium Longiflorum", *Hort Science* 11(3): (1976) pp. 199–200; and A. N. Roberts and L. H. Fuchigami, "New Lily Deflowering Treatment Shows Promise", *Flor. Rev.* 151: 25–26 (1972). In addition, the surfactant Prune S, which is commercially available from KAO Food Corporation, Japan, has recently been reported to be an effective chemical flower pruner for peanut plants. However, the prior art does not suggest that any of the surfactants or methods of the present invention described herein may be used to effectively and efficiently inhibit the opening of pineapple flowers.

SUMMARY AND OBJECTS OF THE INVENTION

Thus, it is an object of the present invention to provide a method for preventing pineapple flowers from opening, which is less costly and more effective than previously reported methods.

A further object of this invention is to provide a method for inhibiting the opening of pineapple flowers using certain surfactants as hereinafter described.

These and other subsidiary objects which will become apparent to those skilled in the art are achieved by the practice of the present invention.

The present invention provides a method for reducing the susceptibility of pineapple fruit to disease which comprises the step of applying an aqueous solution of a non-phytotoxic, and nonionic or anionic surfactant to the pineapple plants in amounts effective to inhibit opening of the pineapple flowers. Preferably, two applications of the aqueous solution are sprayed onto the hearts of the pineapple plants.

The surfactant is preferably a nonionic surfactant selected from the group consisting of polyoxyethylene alkyl ethers or an anionic surfactant selected from the group consisting of sulfonic acids and the salts thereof, in particular the sodium and calcium salts of alkylbenzene sulfonates, dialkyl sulfosuccinates, and mixture thereof.

DETAILED DESCRIPTION OF THE INVENTION

While the invention is susceptible to various modifications and alternative forms, there will be described herein in detail the preferred embodiments. This invention is based on the discovery that certain surfactants are effective for increasing the resistance of pineapple plants to disease. Accomplishment of this desirable goal is realized by applying sufficient amounts of the surfactant onto the pineapple plant, to inhibit opening of the pineapple flowers. The surfactant is applied as a solution, which is preferably aqueous, by such methods as by spraying or pouring so as to throughly coat the young inflorescences.

As understood by those skilled in the art, the term "surfactant" is used to describe a variety of amphipathic molecules composed of separated groups having opposing solubilizing tendencies. For example, a surfactant may contain an oil-soluble hydrocarbon chain separated by a suitable degree from a water-soluble ionic group. C. Arno and J. Lynn, Jr., *Surfactants and Detersive Systems,* vol. 22 *Encyclopedia of Chemical Technology* 3rd ed. (Kirk-Othmer 1983), pp. 332–336.

Surfactants are generally classified according to the charge of the larger group in the molecule. In anionic surfactants, this moiety carries a negative charge, while in cationic surfactants the charge is positive. Nonionic surfactants carry no charge, and the solubilizing contribution is usually supplied by a chain of ethylene oxide groups. In amphoteric surfactants, on the other hand, solubilization is provided by the presence of both positively and negatively charged groups.

Tests have indicated that only certain of the many surfactants which are known, or mixture thereof, are suitable for use in the present invention. The surfactant, which must not be non phytotoxic in the usual concentrations in which it is applied, is preferably a nonionic surfactant selected from the group consisting of polyoxyethylene alkyl ethers, or an anionic surfactant selected from the group consisting of sulfonic acids and the salts thereof (including sulfonic acid esters) in particular alkylbenzenesulfonates, dialkyl sulfosuccinates, and mixtures thereof. The calcium and sodium salts of these anionic sulfonates are preferred.

The following surfactants have been found particularly effective at inhibiting the opening of pineapple flowers and are most preferred:

1. AEROSOL ® OT-75 (SURTEN), a sodium dioctyl sulfosuccinate commercially available from Cyanamid;
2. TOXIMUL S ™, a nonionic emulsifier commercially available from Stepan Chemical Co., U.S.;
3. PRUNE S ™, a calcium alkylbenzenesulfonate commercially available from KAO Foods Corp., Japan;

4. AGRISOL A-1431 TM, a polyoxyethylene alkyl-lauryl ether, which is a nonionic surfactant commercially available from KAO Food Corp., Japan;
5. AGRISOL S-100 TM, a polyoxyethylene alkyl ether commercially available from KAO Food Corp., Japan; and
6. laundry detergent, such as TEMPO ®, which contains alkylbenzenesulfonic acid, caustic soda, sodium triphosphate, toluene, and calcium carbonate and is commercially available from Lever Industrial, Manila, Philippines.

As understood by those skilled in the art, the term "laundry detergent" is used to describe a variety of materials comprised of anionic surfactants having the general formula of $RCOO^-M^+$, wherein R is a straight chain hydrocarbon in the $C_9$–$C_{21}$ range and $M^+$ is a metal or ammonium ion; inorganic acids, bases, and salts, including builders which do not contribute detergency but provide other functions such as regulating density; and organic additives that enhance detergency, foaming power, and the like.

Other surfactants, such as TRITON X-45 TM (an octyl phenoxy ethanol having 5 mol ethylene oxide, commercially available from Rohm and Haas), TOXIMUL H TM (a blend of calcium sulfonate and nonionic surfactant commercially available from Stepan Chemical Co., U.S.), and TOXIMUL D TM (a blend of calcium sulfonate and nonionic surfactant, commercially available from Stepan Chemical Co., U.S.) which are contemplated to fall within the scope of the invention, were found to be useful but less effective in inhibiting the opening of pineapple flowers than the preferred surfactants listed above.

For reducing the susceptibility of pineapple fruit to disease according to the invention, an aqueous solution having a surfactant concentration of from about 0.5 to 1% by weight is preferably utilized. The aqueous solution is preferably sprayed with a knapsack or boom sprayer onto the hearts of the pineapple plants so as to ensure thorough coverage of the young inflorescences. Preferably, two applications of the aqueous solution are sprayed onto the pineapple plants at a rate of about 400 gallons per acre. Most preferably, the aqueous solution is first applied about 5 days before the start of flowering (antithesis) and then reapplied about 5 to 7 days later.

By treating pineapple plants in accordance with the invention, the dormant pineapple buds are inhibited or prevented from opening. Because significantly fewer open flowers are available to serve as the main entrance points for the microorganisms causing pineapple disease, the susceptibilities of the pineapple fruits to disease are reduced.

Additionally, it has been found that only two applications of the surfactants described herein are necessary during the flowering period to achieve results equivalent to those obtained using ten applications of ethrel. Thus, the present invention provides a method that is effective and less costly than previously reported methods.

What is claimed is:

1. A method for reducing the susceptibility of pineapple fruit to disease which comprises the step of applying an aqueous solution of a non-phytotoxic, and nonionic or anionic surfactant to the hearts of pineapple plants in amounts effective to inhibit opening of the pineapple flowers.

2. A method according to claim 1, wherein the aqueous solution is from about 0.5 to about 1% surfactant by weight.

3. A method according to claim 1, wherein two applications of the aqueous solution are sprayed onto the hearts of the pineapple plants.

4. A method according to claim 3, wherein the first application is applied about 5 days before the start of flowering, and the second application is applied about 5 to 7 days later.

5. A method according to claim 2, wherein the aqueous solution is applied at a rate of about 400 gallons per acre.

6. A method according to claim 1, wherein the surfactant is a nonionic surfactant selected from the group consisting of polyoxyethylene alkylethers.

7. A method according to claim 1, wherein the surfactant is an anionic surfactant selected from the group consisting of sulfonic acids and salts thereof.

8. A method according to claim 7, wherein the anionic surfactant is selected from the group consisting of alkylbenzenesulfonates, dialkyl sulfosuccinates, and mixtures thereof.

9. A method according to claim 1, wherein the surfactant is selected from the group consisting of AEROSOL ® 07-75, TOXIMUL S TM, PRUNE S TM, AGRISOL A-1431 TM, AGRISOL S-100 TM, laundry detergent, and mixtures thereof.

* * * * *